United States Patent [19]

Gross

[11] 3,995,021

[45] Nov. 30, 1976

[54] ANTIGENS OF 5,5′ ALKYLPHENYL BARBITURIC ACIDS AND RELATED HYDANTOIN COMPOUNDS

[75] Inventor: Stanley Joseph Gross, Encino, Calif.

[73] Assignee: Biological Developments, Inc., Encino, Calif.

[22] Filed: Jan. 21, 1975

[21] Appl. No.: 543,012

Related U.S. Application Data

[63] Continuation-in-part of Ser. No. 253,632, May 15, 1972, Ser. No. 462,517, April 19, 1974, Ser. No. 160,559, July 7, 1971, and Ser. No. 480,097, June 17, 1974, said Ser. No. 253,632, is a continuation-in-part of Ser. No. 89,929, Nov. 16, 1970, abandoned, which is a continuation-in-part of Ser. No. 45,558, June 11, 1970, abandoned, said Ser. No. 462,517, is a continuation of said Ser. No. 89,929, said Ser. No. 160,559, is a continuation-in-part of said Ser. No. 89,292, said Ser. No. 480,097, is a continuation of Ser. No. 160,150, July 6, 1971, which is a continuation-in-part of said Ser. No. 89,929.

[52] U.S. Cl. ............................ 424/1.5; 260/112 R; 424/12; 424/85; 424/88

[51] Int. Cl.² .................. G21H 5/02; A61K 39/00

[58] Field of Search ............ 260/112 R, 257, 309.5; 424/1, 12, 85, 88

[56] References Cited

UNITED STATES PATENTS

| | | | |
|---|---|---|---|
| 3,766,162 | 10/1973 | Spector | 424/12 X |
| 3,888,866 | 6/1975 | Leute et al. | 424/12 X |
| 3,901,654 | 8/1975 | Gross | 424/1 X |

*Primary Examiner*—Benjamin R. Padgett
*Assistant Examiner*—Christine M. Nucker
*Attorney, Agent, or Firm*—McAulay, Fields, Fisher & Goldstein

[57] ABSTRACT

Antigens comprising 5,5′-alkylphenyl barbituric acid haptens and related 5,5′-phenylhydantoin haptens coupled to a carrier through an azo group connected meta or para on the phenyl ring are prepared by diazotization of the corresponding amine. Specific antibodies are raised in animals and used in radioimmuno assays for the corresponding hapten.

12 Claims, No Drawings

ANTIGENS OF 5,5′ ALKYLPHENYL BARBITURIC ACIDS AND RELATED HYDANTOIN COMPOUNDS

CROSS-REFERENCE TO RELATED APPLICATIONS

This application is a continuation-in-part of my copending application Ser. No. 253,632, filed May 15, 1972, which was a continuation-in-part of co-pending application Ser. No. 89,929, filed Nov. 16, 1970, now abandoned, which, in turn, was a continuation-in-part of my application Ser. No. 45,558, filed June 11, 1970, now abandoned; of my co-pending application Ser. No. 462,517, filed Apr. 19, 1974, which was a continuation of application Ser. No. 89,929, aforereferenced; of my co-pending application Ser. No. 160,559, filed July 7, 1971, which was a continuation-in-part of application Ser. No. 89,929, aforereferenced; and of my co-pending application Ser. No. 480,097, filed June 17, 1974, which is a continuation of application Ser. No. 160,150, filed July 6, 1971, which was a continuation-in-part of application Ser. No. 89,929, aforereferenced.

BACKGROUND OF THE INVENTION

1. Field of the Invention

This invention relates to immunochemicalassaying. Immunochemicalassays are proving of immense value in medicine and biology for assaying liquid samples, especially, for example, body fluid samples such as blood or urine, because of the sensitivity and specificity of such assays. The present invention is concerned with assaying for phenobarbital, phenyl methyl barbituric acid and mephobarbital and related hydrantoin compounds, including diphenyl hydantoin. Accurate assay of these substances is of the utmost value in medical diagnosis and control of drug abuse.

In immunoassaying procedures, for a given target compound, a synthetic antigen is generally first prepared. Heretofore, this has usually been accomplished by coupling the target compound, through a coupling group to a carrier which confers antigenicity to the entire compound. The compound coupled to the carrier is usually known as a hapten and, when coupled, it functions as an antigenic determinant so that the antibodies produced will bind with the hapten. Thus, the antibodies produced should have a distinct and unique character, such that they will bind with only a specific compound or class of compounds. The objective in devising the synthetic hapten-carrier conjugate is to provide a compound which will generate antibodies that are specific to the target compound.

Antibodies are prepared by injecting the synthetic hapten-carrier conjugate into mammals and recovering blood serum from the mammals after they have had time to generate antibodies. Typical mammals are rabbits and goats.

The principal problem is usually that of synthesizing antigens that are capable of producing sufficiently specific antibodies. Biological fluids such as blood and urine frequently contain very closely related compounds and it is common for antibodies to be unable to distinguish the target compound from close relatives, or sometimes even from distant ones. The antibody is then considered to be a poor one and is said to have low specificity and high cross-reactivity.

The assay itself is commonly a competitive binding assay. In a useful embodiment of such an assay, the target compound, which is not necessarily extracted, is allowed to compete with known quantities of a labeled standard to bind with a known quantity of specific antibody. From measurement of the proportion of the labeling in the standard-antibody complex that results, the amount of target compound present can be calculated. Radioactive labeling is particularly convenient. Fluorescence perturbation and electron spin resonance have been used in the art. Normally it is necessary to remove any unreacted labeled standard, before making the determination on the antibody complex, although theoretically, the determination could be made on the removed unreacted portion of the standard.

2. Prior Art

Spector U.S. Pat. No. 3,766,162 discloses a radioimmunoassay for barbituric acids using antibodies generated by synthetic antigens, the subject of the patent. The antigen comprises a barbituric acid hapten coupled to a protein carrier. The barbituric acid has a 5-substituent and is coupled to the carrier by a peptide bond to that substituent. Spector reports, col. 5, lines 41–43, that the antibody will not differentiate between barbituric acids having different substituents in the 5 position.

Spector mentions phenyl as an example of aryl groups among the list of possible derivatives at the 5 position (col. 3, line 5) and states that the bartituric acid derivative may be disubstituted.

The listing of 5-position derivatives in column 3 of Spector also includes mention of other aromatic groups, namely (lines 13–14) carboxy-substituted aralkyl groups e.g. p-carboxy-benzyl, p-carboxy-α-methylbenzyl. It will be noted that these groups have an alkyl group connecting the phenyl ring to the barbituric acid ring.

It is clear that the point of coupling is to a carboxy or amino group on a 5 substituent (col. 2 lines 68–71) and many of the possible derivatives listed in column 3 carry carboxyl groups. The Spector patent (col. 3, lines 14–19) states that these carboxyls can be converted to amines.

The general teaching of Spector is that antibodies produced from these antigens will bind with barbituric acids that are mono or di-substituted in the 5 position (col. 2 lines 33–36; col 4 lines 45–57; col. 5 lines 12–15 and 36–55; and col. 7 lines 3–10). The antibodies generally bind with barbituric acids substituted in the 5-position while being able to discriminate some variations elsewhere in the molecule, notably substitution at the 1 or 3 position and a 2-thio derivative (col. 5 lines 36–55 and Col. 7 lines 3–10). It appears that antibodies produced from any one antigen can be expected to bind with any 5-substituted 1, 3-unsubstituted barbituric acid. The particular character of the 5-substituent does not appear to be important. Thus it may be selected from the long list of derivative groups recited at the head of column 3. Further, these derivatives can be extended by reaction of a carboxyl derivative with a diamine, col. 3 lines 19–23.

Column 4, lines 54–57, states inter alia that the antibody will selectively complex with "the substituted barbituric acid". Presumably this is "The barbituric acid derivative" described in the paragraph at column 2, line 64, which according to lines 68–71 must include on the 5-substituent a carboxyl or amino group. There is however no report of the complexing of antibody with such a carboxyl or amino containing barbituric acid.

This invention differs from the Spector patent in that coupling to the carrier is through the meta or para position on the phenyl ring of the hapten compound. The resulting antigen raises an antibody which is specific to the respective hapten compound used. The Spector coupling is to a carboxyl or amino group in the 5 position and the resulting antibodies are not specific to either of the three barbituric acid target haptens, such as phenobarbital, included in this invention.

In fact, as Spector states (col. 5, lines 41–43): "the antibody will not differentiate between barbituric acids having different substituents in the 5-position."

BRIEF DESCRIPTION OF THE INVENTION

This invention provides an antigen based on a target hapten comprising the 5-alkyl, 5-phenyl barbituric acids of phenobarbital, phenyl methyl barbituric acid and mephobarbital or comprising related 5, 5' phenyl hydantoin compounds hereinafter described.

The target hapten is coupled to a carrier (which confers antigenicity) through a meta or para azo group on the phenyl ring.

An antibody raised in animals, using an antigen of this invention, shows improved specificity when used in an assay for the target hapten.

The barbituric acid targets haptens of this invention are disubstituted 5-alkyl-5' -phenyl barbituric acids selected from the class consisting of:

phenobarbital:

(1) 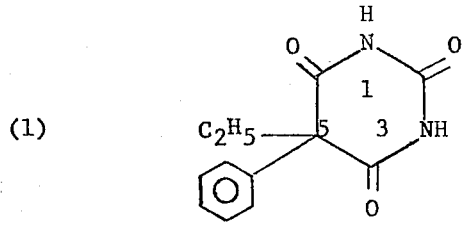

phenylmethyl barbituric acid:

(2) 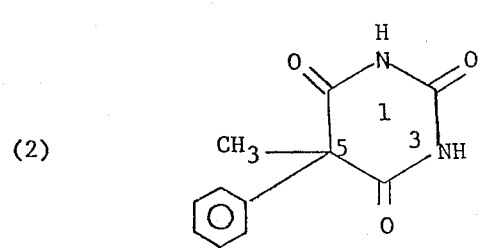

and mephobarbital:

(3) 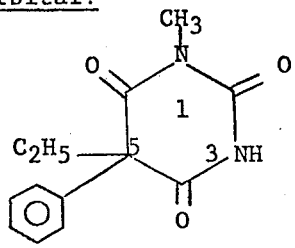

The phenyl hydantoin target haptens of this invention have the following formula:

(4) 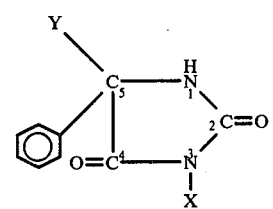

in which X is hydrogen, methyl or ethyl and Y is hydrogen, ethyl or phenyl.

By way of advance over the Spector patent (U.S. Pat. No. 3,766,162) this invention provides an antigen in which a 5-alkyl-5'-phenyl barbituric acid, coupled to a carrier through an azo group meta or para on the phenyl ring, provides an antibody which shows substantial discrimination of barbituric acids having various substituents at the 5 position.

The Spector patent does not contemplate such discrimination or such method of coupling.

DETAILED DESCRIPTION OF THE INVENTION

An antigen according to this invention may be prepared by selecting a phenyl substituted barbituric acid or hydantoin hapten target compound corresponding to one of the formulas (1)–(4) set forth above and introducing an amino group meta or para on the phenyl ring. The amino group is then diazotized and coupled to a diazotizable carbon of an aromatic ring which is coupled to a carrier to confer antigenicity.

Conveniently, the aromatic ring will already be present on the carrier, as is the case with, for instance, natural proteins containing tyrosyl or histidyl groups, and the coupling in that case would be made directly to the carrier. However, the ring could be introduced on the carrier before coupling, or the diazonium salt of the hapten could be coupled to a suitable aromatic compound such as a hydroxyaromatic acid, e.g. salicyclic acid or p-hydroxyaniline, which may then by conventional means be coupled to the carrier.

Preparation of those amines of the phenyl barbituric acids and phenyl hydantoins is known to the art. For example, Butler in *J.P.E.T.* Vol. 116 (1956) pp 326–7 describes the nitration of phenobarbital followed by its reduction to the amino. Some exemplary conditions for nitration, reduction and carrier coupling are as follows. These procedures, while described in terms of phenobarbital, are applicable to all the compounds of formulas (1)–(4).

Nitration

This is generally a standard organic chemistry nitration of a phenyl ring. Some practical details will be mentioned however, as exemplary, to demonstrate the reaction.

The temperature is controlled throughout the nitration to lie between −10° and 10° C to reduce the vigor of the reaction. From 1 to 30 percent, by weight, and preferably around 20 percent of the alkylphenyl barbituric acid is dissolved in concentrated sulfuric acid and up to 20 percent molar excess of fuming nitric acid is added, dropwise, maintaining the temperature at from −10° to 0° C. The mixture is stirred for from 30 minutes to 4 hours to complete the reaction. It is then allowed to come to room temperature, which may complete the reaction if the stirring was inadequate, and poured onto an ice/water mixture to precipitate the reaction product, 5-alkyl-5′ nitrophenyl barbituric acid. This is filtered off and preferably recrystallized for which acetone/ether can be used. Normally, for specificity of the antibody, a single isomer will be desired and, accordingly, fractional crystallization may be necessary to separate the meta and para isomers. When an isomeric mixture is produced, the separation can, if desired, be made after the next reduction step.

Reduction

This, too, is generally a standard organic chemistry reduction or hydrogenation of a nitrophenyl to the amine, and any known procedure can be used provided, of course, that the phenyl ring is not hydrogenated as well. Some possible practical details will however be described, as exemplary, to demonstrate the step.

From 1 to 10, and preferably about 4 percent, by weight, of the 5-alkyl-5′-nitrophenyl barbituric acid from the preceding step is dissolved in ethanol and a palladium/carbon catalyst is added. The mixture is then shaken at room temperature under from 1 to 5, and preferably about 2, atmospheres gauge of hydrogen. This is continued to completion as indicated by measurement of the quantity of hydrogen absorbed. Also, the solution clarifies from an initially yellowish color as the reaction proceeds.

The catalyst is filtered off, the solvent evaporated and the 5-alkyl 5′-aminophenyl barbituric acid recovered by recrystallization from an ether/petroleum ether solvent. The product can be fractionally crystallized if necessary.

Diazotization

This is a standard reaction and the conditions and reagents known to be effective can be employed. However, some exemplary conditions will be described. In this reaction the 5-alkyl 5′-aminophenyl barbituric acid is diazotized and coupled to the aromatic ring of the carrier.

Two aqueous solutions are prepared at 0°–5° C. One is a solution of the derivatized barbituric acid acidified with HCl to a $p^H$ of from 0.5 to 2.0, preferably from 1.0 to 1.5. The concentration is dictated by convenience and solubility, being from about 0.1 to 10 percent by weight, barbituric acid with approximately 4 percent being preferred. The other solution is a simple, aqueous solution of sodium nitrite which, for example, can be a 1 percent solution.

At a temperature of from 0° to 5° C, the sodium nitrite solution is added, dropwise, to the barbituric acid solution, to an end point with potassium iodide-starch paper. Excess nitrous acid is decomposed with sulfamic acid. Under the acid conditions, the diazonium compound forms the salt.

Carrier coupling

The carrier is dissolved at about 0.1 weight percent preferably in an aqueous medium at a $p^H$ adjusted to be from 9 to 11 with sodium hydroxide. The diazonium solution from the previous step is added, dropwise to this solution at a temperature maintained at from 0° to 5° C, maintaining also the pH at from 9 to 11 with sodium hydroxide. The mixture is stirred to completion of the reaction which takes from about 20 minutes to 1 hour.

Desirably the product is dialyzed for from 4 to 10 days with a phosphate buffer to reduce the $p^H$ to a physiologically compatible level of from 7.4 to 7.6. An injectable solution can then be obtained that can be used directly for raising antibodies. Alternatively, the solution can be lyophilized to recover the solid carrier-diazo-5 alkyl -5′ phenyl barbituric acids synthetic antigen conjugate.

In order to be capable of conferring antigenicity, the carrier will normally be antigenic itself, although it may be an incomplete antigen, becoming complete only when coupled to the hapten. To be antigenic, the carrier must be an immunogenic substance, that term being used to refer to a substance capable of eliciting production of antibodies in a host animal to which the immunogenic substance is administered. While, in general, it is believed that the terms "carrier" and "immunogenic substances" are clearly understood in the art, and the discussion herein is not meant to modify the ordinary significance of the terms, further definition is provided here for a clearer understanding of the development.

The animal to which the antigenic substance is administered must be one having an effective immunological system. The immunogenic substances must be "foreign" to the animal, in the sense of not being "self." That is, the immunogenic substance administered must not be one which is a natural body substance of the animal and would, therefore, be accordingly tolerated by the animal's immunological system.

Generally, the antibodies elicited upon injection of the immunogenic substance into the animal will be generated by the host animal and will be capable of reacting or binding with the antigen in an observable and selective way. Thus, the antibodies will display some degree of discrimination between the administered immunogenic substance and other immunogenic materials.

The requirements for immunogenicity are not fully understood. However, it appears that for a molecule to be antigenic, it must have a certain complexity and a certain minimal molecular weight. Formerly, it was thought that the lower molecular weight limit to confer antigenicity was about 5,000. However, antigenicity has recently been demonstrated with molecules having molecular weights as low as 2,000. Molecular weights of 3,000 and more appear to be more realistic as a lower limit for immunogenicity, and approximately 6,000 or more is preferred.

Exemplary immunogenic carrier materials are those set forth in Cremer et al., "Methods in Immunology" (1963), W. A. Benjamin Inc., New York, pages 65 to 113. That disclosure is herein incorporated by reference. The carrier material can be a natural or synthetic substance, provided that it is an antigen or a partial antigen. For example, the carrier material can be a protein, a glycoprotein, a nucleoprotein, a polypeptide, a polysaccharide, a lipopolysaccharide, or a polyaminoacid. An example of an apparently incomplete antigen is the polypeptide glucagon.

A preferred class of natural carrier materials is the proteins. Proteins can be expected to have a molecular weight in excess of 5,000, commonly in the range of from 34,000 to 5,000,000. Specific examples of such natural proteins are bovine serum albumin (BSA), keyhole limpet hemocyanin (KLH), human immunogammaglobulin (HGG), and thyroglobulin.

Exemplary of the synthetic carrier is a polyaminoacid, polylysine. Where the synthetic antigen comprises a partially antigenic carrier conjugated with a hapten, it will generally be desirable for the conjugate to have a molecular weight in excess of 6,000, although somewhat lower molecular weight may be useful.

Preferably, the natural carrier has some solubility in water or aqueous alcohol. Also preferably, the synthetic antigen is water soluble. Desirably, the carriers are non-toxic to the animals to be used for generating antibodies.

The carrier must have a, or preferably a plurality of, functional moieties by means of which it can be coupled. Of course, these groups can be introduced synthetically. Preferably, in practicing the present invention, a single carrier moiety should have a plurality of hapten moieties coupled to it, for example, from about 10 to about 70. In general, the maximum possible number of haptenic moieties per carrier molecule is preferred. Subject to steric hindrance, the maximum number will be determined by the number of reactive coupling groups on the carrier. For example, with BSA, it appears that the maximum number of haptenic moieties that can be coupled is between 60 and 70.

In preparing the antigens of the invention it is, as a practical matter, very desirable to obtain them with a high degree of purity. High antigen purity appears to be an important requisite for optimum antibody production. Accordingly, it is desirable for the process to provide for isolation of the antigen from antigenically distinct materials. The latter will normally be undesired large molecules that may confuse the immune response of animals used for producing antibodies. A feature of the process of the invention is that it is designed to minimize the formation of such undesired antigenically distinct materials.

Removal of small molecule reactants and reaction products is generally desirable, particularly if they are likely to couple to the carrier. However, some small molecule substances may be useful, for example for $p^H$ control. Thus a convenient end-product form in which to recover the antigen is in a buffered aqueous solution which is suitable for direct administration to animals.

The process of the invention can accordingly include a number of purification steps using well-known techniques such as column chromatography, dialysis and recrystallization. Further it will be generally desirable to use high purity reactants. For a natural protein carrier commercially available high purity fractions are desirable.

Antibodies can be raised by administration of an antigen of the invention to mammals such as goats or rabbits, using known immunization procedures. Usually a buffered solution of the antigen accompanied by Freund's adjuvant is injected sub-cutaneously at multiple sites. A number of such administrations at intervals of days or weeks is usually necessary. A number of animals, for example from three to twenty, is so treated with the expectation that only a small proportion will produce good antibodies. However, one goat producing high quality antibodies can provide sufficient for several hundred thousand assays. The antibody is recovered from the animals after some weeks or months.

The assay, according to the present invention, is an immunochemical method of assaying for the presence of a target according to the present invention, that target being contained in a sample. The method employs an antibody obtained by the immunologic response of a vertebrate animal to administration of an antigen according to the present invention, and the antibody is specific to the target. Further, the assay employs a standard, the standard and target competitively binding with the antibody to form an antibody-standard complex and an antibody-target complex. The antibody-standard complex has an artificially introduced radiation label so that the complex can be assayed quantitatively by measurement of the radiation emanating from it. In order for the method to be properly employed, the affinities of the antibody for the standard and for the target must be known quantitatively. In employing the method, a known quantity of the sample and a known quantity of the standard are allowed to compete for binding with a known quantity of the antibody. The radiation emanating from the antibody-standard complex so formed is determined so that the quantity of antibody-bound standard can be calculated and the quantity of target in the sample can be deduced. This deduction is carried out by attributing any difference between the quantity of bound standard determined and the quantity expected, based on the known binding characteristics of the antibody, to binding of the antibody with the target.

In an embodiment of the assaying procedure, the introduced label is radioactive and the antibody-standard is separated from any non-complexed, labeled material after allowing competition binding and before determination of the radiation emanated.

In another embodiment of the assaying method, the introduced label is fluorescent and the standard is provided with a chemical moiety giving it a fluorescence spectrum overlapping the natural fluorescence spectrum of the antibody. The complex can then be assayed by measurement of the perturbation of the antibody fluorescence due to binding with the standard.

The standard is a substance known to bind with the antibody and can be, for example, the target, the antigen used to raise the antibody, or the hapten used to make the antigen. Similarly, it can be a similar antigen having the same hapten bound to a different carrier, but at the same position on the hapten. Conveniently, where the radiation constitutes radioactive emission, such as beta or gamma rays, the standard can carry the radioactive label in the form of a radioactive isotope, e.g., tritium, $I^{125}$, or $C^{14}$, although, as an alternative, the antibody can be labeled.

When separation of the complex from the unreacted standard is necessary, as is normally the case with radioactive labeling, this can be effected by phase separation, insolubilizing of one of the components to be separated, etc. Thus, with a labeled antibody, the use of an antigenic standard having a plurality of antibody binding sites causes the antibody-standard complex to precipitate while, if the target is a small molecule, the antibody-target complex will remain in solution. Alternatively, the antibody can be insolubilized, as described elsewhere in the specification, and the standard labeled, so that unreacted standard stays in solution and can easily be separated from the complex.

One example of such a separation is the addition of saturated ammonium sulfate to the complexed mixture. The mixture, with the added ammonium sulfate, is then centrifuged which results in deposition of most of the protein, including the antibody-standard complex. The antibody-standard complex can then be removed as a solid and measurement carried out on this solid. Alternatively, the uncomplexed liquid standard is subjected to measurement or radiation emanation.

A further possibility is to absorb the standard with dextran-charcoal, after allowing for competition binding, and to then make the scintillation count for radiation on the liquid phase containing the antibody-standard complex following separation of the solid phase which contains the unreacted standard. In this case, the standard is labeled and is a small molecule, especially a radioactive isotope labeled target molecule.

While the count for radiation is normally made upon the antibody-standard complex, as this is either more convenient or is believed to reduce experimental error, it will be clear that where there is a separation of unbound, labeled material from the antibody-standard complex, the determination of the radiation emanating from the antibody-standard complex can equally well be made by measuring the radiation emanating from the unreacted, labeled material. From this measurement, the difference from the known amount of labeled material added can be calculated.

The term "radiation" is used in an ordinary dictionary sense and refers to energetic emissions originating from individual atoms or molecules which are generally attributed to internal changes within the atom or molecule. These emissions are in contrast to physical phenomena, such as, for example, precipitations which are the result of the inter-molecular or inter-atomic effects, and may require a large-scale cooperation of a great number of atoms or molecules to be meaningfully expressed. Radiation is significant for immunoassays as it provides a means of remotely monitoring the behavior of very small quantities of matter.

Thus, in addition to energetic emissions, radiation includes such phenomena as fluorescence and electron spin resonance. Fluorescence usually requires excitation by exposure to ultraviolet light, but the product is radiation. Thus, energy, usually in the form of light, is emitted as a result of intra-molecular change.

Where fluorescence is the form of radiation measured, it is feasible for the assay to be conducted without any separation of materials. Thus, antibodies, which are naturally fluorescent, have an absorption spectrum and an emission spectrum. If the standard chosen is a molecule having, as a label, a chemical group which fluoresces in spectra overlapping the antibody, then, when the standard complexes with the antibody, the natural fluorescence of the antibody is perturbed by that of the standard, and this perturbation can be measured. When the emission spectrum of the standard overlaps the absorption spectrum of the antibody, fluorescence enhancement will be observed from the complex at the antibody emission wavelength, and when the absorption spectrum of the standard overlaps the emission spectrum of the antibody, fluorescence quenching will be observed from the complex at the antibody emission wavelength. Comparable effects can be displayed using polarization perturbation.

Electron spin resonance labeled assays can also be conducted without the need for separation. A paramagnetic labeling group, such as a nitroxide ring, is attached, for example, to the standard. When subjected to a microwave frequency magnetic field, an electron spin resonance spectrometer can detect distinct resonance peaks characteristic of the nitroxide ring label. When the standard combines with antibody, these peaks are substantially extinguished, providing a direct indication of the degree of binding.

The following examples illustrate the invention.

EXAMPLE 1 a. Synthesis of 5- (m-nitrophenyl) 5-ethylbarbituric acid (m-nitrophenobarbital)

10 gm. of phenobarbital is added to 40 ml. of ice-cold, concentrated sulfuric acid. A nitrating mixture of 2.2 mls. of fuming nitric acid in 10 ml. concentrated sulfuric acid is added drop-wise to the stirred reaction mixture using a mechanical stirrer while maintaining the temperature between −10° to 3° C. Stirring is continued for an hour after the nitrating mixture is added. The reaction mixture is poured into 600 ml. of an ice-water mixture and filtered when cold. The white precipitate is washed repeatedly with water until neutral to litmus and then dried under vacuum.

Several recrystallizations of the crude material from 95% ethanol gave 5- (m-nitrophenyl) -5-ethyl barbituric acid with a melting point of 283°–284° C.

b. Preparation of 5-(m-aminophenyl)-5-ethyl barbituric acid (m-aminophenobarbital)

2 gm. of m-nitrophenobarbital from (a) is suspended in 25 ml. ethanol and hydrogenated at 30 psig. and room temperature using 100 mg. Pd/C (10%) as catalyst. The hydrogenated solution is filtered to remove catalyst and the solvent is removed on a rotary evaporator. Several crystallizations from an ethanol-ether solution yield pure 5-(m-aminophenyl)-5-ethyl barbituric acid with a melting point of 208°–209° C.

c. Coupling of m-aminophenobarbital to keyhole limpet hemocyanin (KLH)

50 mg of m-aminophenobarbital from (b) is dissolved in 1 ml. of 1N HCL and the solution cooled to 0°–5° C. To it is added a cold (0°–5° C) solution of sodium nitrite (15 mg) in 0.5 ml water to an end point with starch iodide paper. Excess nitrous acid is decomposed with a few crystals of sulfamic acid. The cold diazonium salt solution is added drop-wise to a cold (0°–5° C) solution of 600 mg. KLH in 10 ml. water adjusted to pH 10.5 with 2N sodium hydroxide. During the addition the pH is maintained between 9 and 11 with 2N sodium hydroxide and the temperature is maintained at 0°–5° C. After the addition is complete the solution is stirred at 0°–5° C for 1 hour at pH 10.5. It is transferred to a dialysis tubing and dialyzed against 6L of 0.5% sodium carbonate for 6 days with daily changes of the sodium carbonate solution.

It is next dialyzed against 6L of pH 7.4–7.6 sodium phosphate buffer for 4 days with daily changes of the buffer solution.

The optical density at 280 nm. is about 1.1 on a 0.1% solution.

EXAMPLE 2

The procedure of paragraph (a) of Example 1 is repeated except for the recrystallization step. The m - and p - nitrobarbital isomers from that procedure were hydrogenated according to the procedure of paragraph (b) of Example 1. P-aminophenobarbital was recovered by repeated recrystallization. It was then coupled to KLH according to the procedure of paragraph (c) of Example 1 to give results equivalent to those obtained in that Example.

EXAMPLE 3

Examples 1 and 2 are successively repeated using equivalent amounts of bovine serum albumin, human immuno gammaglobulin and thyroglobulin in place of the KLH. Equivalent results are obtained.

EXAMPLE 4

The procedures of Example 1, 2 and 3 are successively repeated using phenyl methyl barbituric acid in place of phenobarbital. In each case equivalent results were obtained.

EXAMPLE 5

The procedures of Examples 1, 2 and 3 are successively repeated using mephobarbital in place of phenobarbital. In each case equivalent results were obtained.

Raising of Antibodies

Approximately 2 mg. doses of antigen in 0.1% aqueous solution with Freund's adjuvant are injected at multiple, subcutaneous sites in rabbits. The injections are repeated at intervals according to known immunization procedure. The rabbits are bled at intervals and the active serum is collected and used without purification.

Radioimmune Assay

The radioimmune assay is performed by incubating various dilutions of antisera obtained from animal bleedings, with tritiated phenobarbital in the presence of buffer at 4° C. After 2 hours a neutral, saturated ammonium sulfate solution is added. The resultant precipitates are sedimented by centrifugation at 3,000 for 15 minutes at 4° C and the supernates are decanted off. Aliquots of 0.5 ml. water and 10 ml. Aquasol are counted for labeled phenobarbital. The addition of increasing amounts of unlabeled phenobarbital to a fixed amount of labeled phenobarbital and antiserum results in a competitive inhibition of the labeled phenobarbital bound to antibody.

This enables a standard curve for the antibody to be established showing the variation of inhibition of binding with concentration.

The specificity of the antibody is then determined by allowing for competitive binding of known concerntrations of the antibody with known concentration of the labeled standard and successive potential cross-reactants. The cross-reactivity is defined according to the method of Abrahams as the relative quantity of target to cross-reactant that produces 50% inhibition multiplied by 100 for percentage.

When the product of Example 1 is used to raise antibodies, and these are used in a radioassay, as previously described, the cross reactivity (at 50% inhibition) of other barbituric acids is as follows:

| Compound | Percent Cross-Reactivity |
|---|---|
| Pentobarbital | 2.2 |
| Secobarbital | 1.8 |
| Amobarbital | 0.6 |
| Thiopental | 0.2 |

EXAMPLE 6

The procedures of Examples 1, 2 and 3 are successively repeated using 5, 5' diphenyl hydantoin. In each case equivalent results were obtained.

Following the procedures of Examples 1 and 2 dinitro diphenyl hydantoin compounds are obtained. In converting the two resulting amine groups to azo groups and coupling to a carrier one of the azo groups couples to the carrier and the other results in a hydroxyl group under the coupling conditions. Small amounts of interlinked high, molecular weight material, in which each azo group is linked to a carrier, may be obtained. Such material may be removed by known chromatographic methods. An antibody raised to the antigen of this Example may be used to assay for diphenyl hydantoin, or any phenolic metabolite of that compound.

EXAMPLE 7

The procedures of Examples 1, 2 and 3 are successively repeated using 5 ethyl, 5' phenyl hydantoin. In each case equivalent results were obtained.

EXAMPLE 8

The procedures of Examples 1, 2 and 3 are successively repeated using 3 methyl, 5 phenyl hydantoin. In each case equivalent results were obtained.

If desired, the antibodies of this invention can be insolubilized, or otherwise supported, on a solid matrix. Examples of materials to which the antibody can be attached are glass, synthetic polymers, synthetic resins, and cellulose. The material to which the antibody is attached or otherwise insolubilized can have an extensive, continuous form, such as a sheet, or it can be in the form of discrete particles of desired size. The antibody can be secured to the material in a number of ways.

Among the methods for attaching or otherwise insolubilizing the antibody to a solid matrix are covalent bonding, van der Waal's forces, hydrogen bonding, etc. Thus, the methods for attaching the antibody to the solid matrix are relatively weak intermolecular forces, covalent bonds, or the adsorptive forces attributable to a porous surface. An example of van der Waal's forces occurs with the adhesion of an antibody to a predominantly hydrophobic plastic surface, such as a polyolefin. Apparently, there is hydrophobic bonding to the hydrophobic amino acid residues of the antibody.

Some of the methods for bonding of the antibody to a solid matrix are discussed in Weliky and Weetall, *Immunochemistry*, Vol. 2, pages 293–322 (1965).

Another method for conveniently covalently bonding the antibody to a solid is by diazotizing available amino groups on the antibody into available, activated, aromatic rings on the solid material.

It may be desirable to modify the material, particularly for the purpose of securing the antibody to it. Thus, for covalent bonding, carbodiimide condensation, with the formation of an amide bond between the antibody and the material, can be used. For this purpose, the material should have available primary, non-aromatic amine groups or carboxyl groups to couple with, respectively, available carboxyl or amino groups on the antibody. An amino glass suitable for this purpose is known. Suitable synthetic resins or polymers may be available, in addition, or existing resins can be modified. Similarly, many derivatized celluloses are known, and cellulose can, in general, be provided with appropriate groups.

In attaching the antibody to the substrate material, it is normally desirable to ensure that the active binding site of the antibody remains available and accessible. This can be facilitated by blocking the site before coupling to the support material, and unblocking thereafter. Blocking can be conveniently effected by complexing the antibody with the hapten for which it is specific and deblocking can be effected with an eluting agent, for example, acetic acid or urea.

For sorption on a porous surface, another method for insolubilizing the antibody on a solid matrix, it is desirable for the pore size of the material, e.g., porous particles, to be selected for optimum accommodation of the antibody.

What is claimed is:

1. A synthetic antigen comprising a phenyl substituted hapten selected from the class consisting of phenobarbital, phenyl methyl barbituric acid, mephobarbital and hydantoin haptens of the following formula:

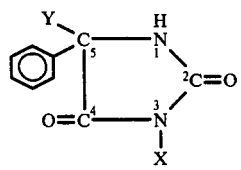

in which X is selected from the class consisting of hydrogen, methyl and ethyl and Y is selected from the class consisting of hydrogen, ethyl and phenyl; coupled through an azo group on the phenyl ring of said hapten to a macromolecule carrier which confers antigenicity, said azo group being selected from the class consisting of a meta azo radical and a para azo radical.

2. The antigen of claim 1 comprising a plurality of the hapten moieties connected to a single carrier moiety.

3. The antigen of claim 2 wherein the carrier is selected from the class consisting of keyhole limpet hemocyanin, bovine serum albumin, human immunogammaglobulin and thyroglobulin and the azo group is connected from the hapten moiety directly to a pendant group of the carrier, said pentant group being selected from the class consisting of a tyrosyl radical and a histidyl radical.

4. Protein meta azo phenobarbital where the protein has a pendant group selected from the class consisting of a tyrosyl radical and a histidyl radical and is connected to the azo group at a diazotizable ring carbon of said pendant group.

5. A method of preparing an antigen according to claim 1 comprising diazotization of a meta or para amino phenyl substituted hapten selected from the class consisting of meta and para aminophenobarbital, meta and para aminophenyl methyl barbituric acid, meta and para aminomephobarbital and meta and para amino phenyl hydantoins of the following formula:

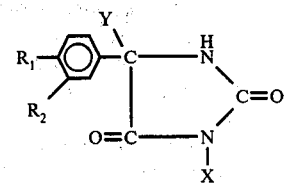

in which X is selected from the class consisting of hydrogen, methyl and ethyl, Y is selected from the class consisting of hydrogen, ethyl, phenyl, meta aminophenyl, and para aminophenyl, $R_1$ is selected from the class consisting of hydrogen and amino and $R_2$ is selected from the class consisting of hydrogen and amino, and $R_1$ and $R_2$ are different; and coupling the resulting diazonium salt to a diazotizable carbon of an aromatic ring having such a carbon, the aromatic ring being coupled to a macromolecule carrier which confers antigenicity.

6. A method according to claim 5 wherein the carrier is a natural protein having a pendant group selected from the class consisting of a tyrosyl radical and a histidyl radical group and the coupling is effected directly to said group.

7. Antibody raised by the antigen of claim 1 and binding with said phenyl substituted hapten.

8. Antibody raised by the antigen of claim 4 and binding with said protein meta azo phenobarbital.

9. An immunochemical method of assaying for the presence of a phenyl substituted target hapten in a sample, said target hapten being selected from the class consisting of phenobarbital, phenylmethyl barbituric acid, mephobartibal and hydantoin haptens of the following formula:

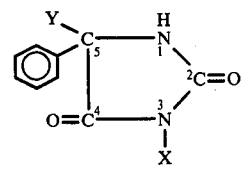

in which X is selected from the class consisting of hydrogen, methyl and ethyl and Y is selected from the class consisting of hydrogen, ethyl and phenyl; wherein said method employs an antibody obtained by the immunologic response of a vertebrate animal to administration of an antigen according to claim 1 and wherein said antibody is specific to the target, said method also employing a standard, the antibody binding with the target to form an antibody-target complex and competitively binding with the standard to form an antibody-standard complex, the antibody-standard complex having an artificially introduced radiation label enabling the complex to be assayed quantitatively by measurement of radiation emanating from it, the affinities of the antibody for the standard and for the target being known quantitatively, said method comprising allowing a known quantity of the sample and a known quantity of the standard to compete for binding with a known quantity of the antibody and determining the radiation emanating from the antibody-standard complex, thereby enabling the quantity of antibody-bound standard to be calculated and the quantity of target in the sample to be deduced.

10. The method of claim 9 wherein the label is radioactive and the antibody-standard complex is separated from any non-complexed labeled material after allowing competition binding and before determination of the emanated radiation.

11. The method of claim 9 wherein the label is fluorescent and the standard is provided with a chemical moiety giving it a fluorescence spectrum overlapping the natural fluorescence spectrum of the antibody, whereby the complex can be assayed by measurement of the perturbation of the antibody fluorescence due to its binding with the standard.

12. The antibody of claim 7 insolubilized by securing it to a solid matrix.

* * * * *